United States Patent [19]

Collington et al.

[11] 4,438,111

[45] Mar. 20, 1984

[54] PROSTANOID COMPOUNDS AND PHARMACEUTICAL FORMULATIONS

[75] Inventors: Eric W. Collington, Welwyn; Peter Hallett, Buntingford; Christopher J. Wallis, Royston, all of England

[73] Assignee: Glaxo Group Limited, London, England

[21] Appl. No.: 419,520

[22] Filed: Sep. 17, 1982

Related U.S. Application Data

[63] Continuation of Ser. No. 223,316, Jan. 8, 1981, abandoned.

[30] Foreign Application Priority Data

Jan. 9, 1980 [GB] United Kingdom ............. 8000698

[51] Int. Cl.³ .................. A61K 31/535; A61K 31/54; C07D 413/12; C07D 417/12
[52] U.S. Cl. ........................................ 424/246; 424/45; 260/244.4; 260/330.3; 424/248.51; 260/330.6; 260/330.9; 424/248.53; 424/248.55; 424/250; 424/267; 424/274; 424/275; 424/285; 544/58.2; 544/58.6; 544/58.7; 544/85; 544/87; 544/109; 544/121; 544/130; 544/141; 544/146; 544/152; 544/357; 544/364; 544/372; 544/379; 546/187; 546/208; 546/213; 546/214; 548/517; 548/527; 542/426; 260/243.3
[58] Field of Search .............. 544/58.2, 58.6, 85, 544/109, 152, 146, 372, 379, 58.7, 87, 121, 130, 141, 357, 364; 546/187, 208, 213, 214; 548/517, 527; 260/243.3, 244.4, 330.9, 330.3, 330.6; 542/426; 424/246, 248.51, 248.55, 274, 275, 248.53, 250, 267, 285, 45

[56] References Cited

U.S. PATENT DOCUMENTS

| | | | |
|---|---|---|---|
| 4,182,903 | 1/1980 | Favara et al. | 562/503 |
| 4,189,606 | 2/1980 | Favara et al. | 562/455 |
| 4,239,778 | 12/1980 | Venton et al. | 424/305 |
| 4,265,891 | 5/1981 | Collington et al. | 424/244 |
| 4,327,092 | 4/1982 | Collington et al. | 424/246 |
| 4,342,756 | 8/1982 | Collington et al. | 424/244 |
| 4,371,530 | 2/1983 | Collington et al. | 424/244 |

FOREIGN PATENT DOCUMENTS 44711 7/1981 European Pat. Off. .

OTHER PUBLICATIONS

Le Breton, G. C. et al., *Proc. Natl. Acad. Sci. USA* 76: 4097 (1979).
Orth, D. et al., *Topics in Current Chemistry* 72: 51–97 (1977).

*Primary Examiner*—Robert W. Ramsuer
*Attorney, Agent, or Firm*—Bernard, Rothwell & Brown

[57] ABSTRACT

Prostanoids are described of the formulae

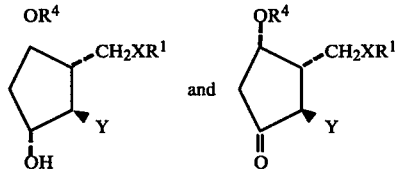

(and the salts thereof) in which:
X is cis or trans—CH=CH— or $CH_2CH_2$—;
$R^1$ is $C_{1-7}$ alkyl terminated by —$COOR^{10}$ where $R^{10}$ is H, $C_{1-6}$ alkyl or aralkyl;
Y is a saturtaed heterocyclic amino group; and
$R^4$ is thienylalkyl or furanylalkyl in which the ring may be substituted.

These compounds inhibit blood platelet aggregation and have bronchodilatory action, and may be formulated for use as anti-asthmatics and antithrombotic agents.

8 Claims, No Drawings

PROSTANOID COMPOUNDS AND PHARMACEUTICAL FORMULATIONS

This is a continuation of application Ser. No. 223,316 filed Jan. 8, 1981, abandoned.

Prostaglandins are a class of naturally occurring cyclopentane derivatives which are biologically active in many physiological systems and they and substances which antagonise their effects are therefore of considerable interest in both human and veterinary medicine.

In view of the activity found in the natural prostaglandins, considerable effort has been directed towards the preparation of synthetic analogues. Many such compounds have been described, and in general it has been reported that these compounds possess activity within the same spectrum as the natural compounds. The synthetic compounds can however have increased selectivity of action, longer duration of activity or different potency, and in some cases they can antagonise the activity of natural prostaglandins.

In most of the synthetic prostanoids previously reported, the side chains have been attached to the cyclopentane ring via carbon atoms, as in the natural prostaglandin structure. We have now found a new class of prostanoid compounds in which the α-side chain has the same or similar structure to that of the natural compounds, while the β-side chain is attached to the ring via a nitrogen atom and the ring is also substituted by certain heteroaralkoxy groups. Compounds in this class have shown prostanoid activity in our tests and in particular they inhibit blood platelet aggregation and have bronchodilatatory action.

The invention provides prostanoids of the general formula (1)

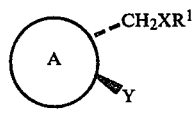

(1)

in which

A represents

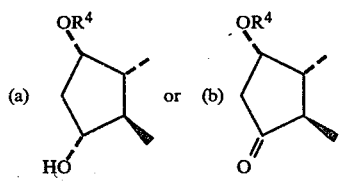

X is cis or trans —CH=CH— or —$(CH_2)_2$—;

$R^1$ is straight or branched $C_{1-7}$ alkyl bearing as a terminal substituent —$COOR^{10}$ where $R^{10}$ is a hydrogen atom, $C_{1-6}$ alkyl or $C_{7-10}$ aralkyl (e.g. benzyl);

Y represents (i) —$NR^2R^3$ where $R^2$ and $R^3$ are the same or different and are each a hydrogen atom, aralkyl having a $C_{1-7}$ alkyl portion or $C_{1-10}$ alkyl, both alkyls being optionally substituted by one or more substituents —$OR^7$ (where $R^7$ is a hydrogen atom, $C_{1-7}$ alkyl, aryl or aralkyl having a $C_{1-4}$ alkyl portion) or —$NR^8R^9$ (where $R^8$ and $R^9$ are the same or different and are each a hydrogen atom or $C_{1-4}$ alkyl, or where —$NR^8R^9$ is a saturated heterocyclic amino group (as defined below for Y); any aryl group in $R^2$ or $R^3$ being optionally substituted by one or more $C_{1-4}$ alkyl or trifluoromethyl groups; always provided that the total number of carbon atoms in the group —$NR^2R^3$ does not exceed 15;

or (ii) a saturated heterocyclic amino group which has 5–8 ring members and (a) optionally contains in the ring —O—, —S—, —$SO_2$, —$NR^{14}$— (where $R^{14}$ is a hydrogen atom, $C_{1-7}$ alkyl or aralkyl having a $C_{1-4}$ alkyl portion), >$C(OH)R^6$ (where $R^6$ is a hydrogen atom, $C_{1-7}$ alkyl, phenyl, or aralkyl having a $C_{1-4}$ alkyl portion); and/or (b) is optionally substituted by one or more $C_{1-4}$ alkyl groups;

$R^4$ is the group:

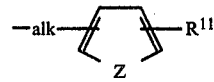

where alk is $C_{1-3}$ alkylene;

Z is O or S;

$R^{11}$ is a hydrogen atom; $C_{1-6}$ alkyl; $C_{1-6}$ alkoxy; aryl (e.g. phenyl) or phenylalkoxy or phenylalkyl having a $C_{1-3}$ alkyl portion (the aryl portion in each case being optionally substituted by $C_{1-3}$ alkyl, $C_{1-3}$ alkoxy or halogen); aryloxy (e.g. phenoxy); $C_{5-7}$ cycloalkyl; halogen or nitro;

and the physiologically acceptable salts thereof.

The formulae used herein are to be understood to depict either or both optical isomers of each of the compounds concerned as well as mixtures of the isomers, including racemates, even though the precise structure as set out only relates to one optical isomer.

Compounds having the ring type (b) are particularly important.

In the group —$CH_2XR^1$, the alkyl portion of the group $R^1$ may for example contain 2–5 carbon atoms (straight or branched) and is preferably —$(CH_2)_3COOR^{10}$. $R^{10}$ is preferably a hydrogen atom or $C_{1-4}$ alkyl, e.g. methyl, particularly hydrogen.

When $R^1$ is terminally substituted by —COOH, the compounds are capable of salt formation with bases, examples of suitable salts being alkali metal (e.g. sodium and potassium), alkaline earth metal (e.g. calcium), ammonium, substituted ammonium (e.g. tromethamine or dimethylaminoethanol), piperazine, morpholine, piperidine and tertiary amine (e.g. triethylamine) salts.

X is preferably —$CH_2CH_2$— or cis —CH=CH—, paticularly the latter.

In the group Y, when one of $R^2$ and $R^3$ is alkyl or substituted alkyl, the alkyl group preferably contains no more than 7 (e.g. 2–7) carbon atoms and preferably has a straight chain. Examples of such groups are n-hexyl and n-heptyl. In such compounds, the other group of $R^2$ or $R^3$ is preferably hydrogen or methyl. When $R^2$ or $R^3$ is an aralkyl group, it may for example be benzyl, phenethyl or phenpentyl.

In the optional substituent —$OR^7$ on $R^2$ or $R^3$, examples of $R^7$ are a hydrogen atom, methyl, n-butyl, phenyl, benzyl and phenethyl. The optional amino substituent —$NR^8R^9$ may for example be —$NH_2$, —NHMe, —NHEt, —$NMe_2$ or —$NEt_2$. These optional substituents may for example be carried at the β-position, as in β-hydroxyalkyl groups. Two —$OR^7$ groups may be present, particularly on an $R^2$ or $R^3$ alkyl group; for example, there may be a hydroxy group at the β-position and a second —$OR^7$ group at the terminal position.

Aryl (e.g. phenyl) groups in $R^2$ and $R^3$ may themselves be substituted, e.g. by $C_{1-4}$ alkyl or trifluoromethyl.

Compounds in which Y is a saturated heterocyclic amino group are however preferred. The types of heterocyclic group which are generally preferred are those in which the ring has 5–8 members and (a) optionally contains —O—, —S—, —SO$_2$— or —NR$^{14}$— and/or (b) is optionally substituted by one or more C$_{1-4}$ alkyl (e.g. methyl) groups. The group may for example have a 5, 6 or 7-membered ring, e.g. pyrrolidino, piperidino, morpholino, piperazino, thiamorpholino, 1-dioxothiamorpholino, homomorpholino and hexamethyleneimino.

Examples of the optional substituents which may be present on a second nitrogen atom in the ring are methyl, ethyl and benzyl. The carbon atoms of the heterocyclic rings may for example be substituted by methyl or ethyl. The group C(OH)R$^6$ may for example be present in a piperidino ring and when R$^6$ is other than hydrogen it may for example be methyl, ethyl or butyl.

Compounds in which Y is a morpholino, dioxothiamorpholino or piperidino group are particularly preferred.

The amino group in the group Y enables the compounds to form salts with inorganic or organic acids, e.g. hydrochlorides, sulphates, acetates, maleates and succinates.

In R$^4$, the alkylene group is preferably methylene and Z is preferably S. Where Z is S, the thienyl group is preferably substituted by C$_{1-3}$ alkyl (e.g. methyl), aryl (e.g. phenyl, optionally substituted by C$_{1-3}$ alkoxy, e.g. methoxy), C$_{5-7}$ cycloalkyl (e.g. cyclohexyl), halogen (e.g. bromine) or phenalkyl (e.g. phenethyl), and where Z is O the furanyl group is preferably substituted by an aryl, e.g. phenyl group. Particularly preferred groups of this type are phenylthienylalkyl and alkoxyphenylthienylalkyl.

A particularly preferred group of compounds has the formula 1(b) where:

X is cis —CH=CH—,

R$^1$ is —(CH$_2$)$_3$COOH,

Y is morpholino, piperidino, or 1-dioxothiamorpholino, and

R$^4$ is methoxyphenylthienylmethyl.

As indicated above, our tests have shown that compounds of formula (1) inhibit blood platelet aggregation and/or have bronchodilatatory activity. The test we have used for bronchodilatation is as described by K. M. Lulich, et al in British Journal of Pharmacology 58, 71–79, (1976) except quinea-pig lung is used instead of cat lung. The test for inhibition of platelet aggregation is as described by G. V. Born in Nature 194, 927–929 (1962) except collagen is used instead of ADP as the pro-aggregatory agent.

The compounds are thus of interest in the treatment of asthma and as antithrombotic agents for use in the treatment and prevention of cardiovascular diseases or conditions such as arteriosclerosis, atherosclerosis and myocardial infarcts. They may be formulated for use in conventional manner, with one or more pharmaceutical carriers.

For oral administration, the pharmaceutical composition may take the form of, for example, tablets, capsules, powders, solutions, syrups, or suspensions prepared by conventional means with acceptable excipients.

The compounds may be formulated for parenteral administration by bolus injections or continuous infusion. Formulations for injections may be presented in unit dosage form in ampoules, or in multi-dose containers, with an added preservative. The compositions may take such forms as suspensions, solutions, or emulsions in oily or aqueous vehicles, and may contain formulatory agents such as suspending, stabilising and/or dispersing agents. Alternatively, the active ingredient may be in powder form for reconstitution before use with a suitable vehicle, e.g. sterile pyrogen-free water.

For administration by inhalation the compounds are conveniently delivered in the form of an aerosol spray presentation from pressurised packs or a nebuliser, or as a cartridge from which the powdered composition may be inhaled with the aid of a suitable device. In the case of a pressurised aerosol the dosage unit may be determined by providing a valve to deliver a metered amount.

For use as antithrombotic agents, the compounds are preferably administered orally, for example in amounts of 0.1 to 10 mg/kg body weight, 1 to 4 times daily. For use in the treatment of asthma, the compounds may also be administered orally in amounts of 0.1 to 10 mg/kg body weight, 1 to 4 times daily; preferably however they are administered by inhalation in the form of aerosols or solutions for nebulisers, at doses varying from 0.3 to 30 mg, 1 to 4 times daily. The compounds may be used in combination with other anti-asthmatic agents. It will be appreciated that the precise dose administered will always depend on the age and condition of the patient.

The compounds of formula (1) may be prepared by selection and adaptation of methods known in prostanoid chemistry (see for example British Patent Specification 2028805A). Method (a) below is particularly important in forming certain prostanoids of the desired class, and other compounds in the class can be prepared from them by known techniques for example using one or more of methods (b) to (k) below.

The following reactions will frequently require the use of (or will conveniently be applied to) starting materials having protected functional groups (e.g. hydroxy). It is to be understood that references to the use of starting materials of a particular structure are intended to include starting materials having protected functional groups. Certain of the reactions described below are capable of affecting other groups in the starting material which are desired in the end product, and this must be taken into account when performing multi-stage reactions.

In the discussion below, the groups X and Y and the various R groups are as defined above except where otherwise indicated.

(a) Compounds of formula (2)

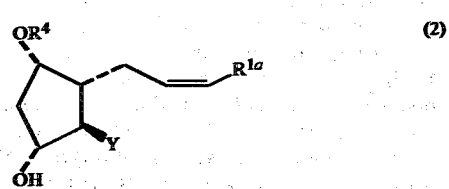

(where R$^{1a}$ is as defined above for R$^1$ where R$^{10}$ is a hydrogen atom) may be prepared by reacting lactols of formula (3) or their aldehyde isomers of formula (3a)

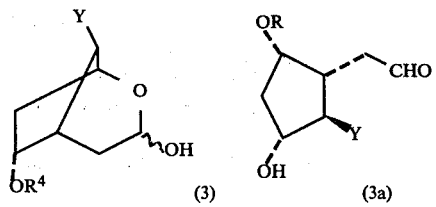

with appropriate Wittig reagents, e.g. a phosphorane of formula $R_3^{12}P=CHR^{1a}$ (where $R^{12}$ is $C_{1-6}$ alkyl or aryl, e.g. monocyclic aryl such as phenyl), or a salt thereof, e.g. the potassium salt. Suitable reaction solvents include hydrocarbons (e.g. benzene and toluene), ethers (e.g. tetrahydrofuran), dialkylsulphoxides (e.g. dimethylsulphoxide), alcohols and halogenated hydrocarbons. The reaction may be carried out at any suitable temperature up to 50° C., preferably at room temperature.

The reaction is particularly suitable for the preparation of compounds in which $R^1$ is terminally substituted by —COOH (in salt form). Any hydroxy group in Y should preferably be in a protected state prior to this reaction. Suitable hydroxy protecting groups are described below. Any —NH$_2$ group present should also be protected, e.g. by t-butoxycarbonyl.

Except as regards the nature of $R^4$, this reaction is the same as process (a) of British Patent Specification 2028805A. The intermediates of formulae (3) and (3a) may thus be prepared by the methods described in that specification, using starting materials containing the desired $R^4$ group.

These starting materials may themselves be prepared by the same general methods as described in Specification 2028805A.

(b) Compounds of ring type (b) may be prepared by oxidising the corresponding hydroxy compound of ring type (a), for example with a $Cr^{VI}$ oxidising reagent, e.g. Jones reagent, at $-10°$ to room temperature, preferably $-10°-0°$, in a solvent such as acetone. Other conventional methods can also be used, for example using dimethylsulphoxide and a suitable electrophilic reagent, such as acetyl bromide, oxalyl chloride, thionyl chloride, or dicyclohexylcarbodiimide in a hydrocarbon solvent such as toluene at low temperature e.g. $-70°$. With the latter reagent, the reaction is preferably carried out in the presence of trifluoroacetic acid or its pyridinium salt.

Other suitable reagents are N-chlorosuccinimidedimethylsulphide complex (used for example in a hydrocarbon solvent, such as toluene, e.g. at 0°-5°), and pyridine-sulphur trioxide complex in dimethylsulphoxide (e.g. at 0° to room temperature).

When the α-side chain has a terminal —COOH group (i.e. when $R^{10}$ is hydrogen), better yields are sometimes obtained by prior protecting the carboxyl group, for example in the form of a trialkyl (e.g. trimethyl or triethyl) silyl ester.

Any other hydroxy group present should be protected in this reaction.

(c) Compounds in which $R^{10}$ is alkyl or aralkyl can be prepared by esterification of the corresponding carboxylic acid (in which $R^{10}$ is hydrogen). Conventional esterification techniques may be used, reaction with a diazoalkane being preferred. The alkyl esters may also be formed by reaction with an appropriate alcohol in the presence of a mineral acid, e.g. hydrochloric or sulphuric acid.

(d) Compounds in which $R^1$ is terminally substituted by a —COOH group can be prepared by saponifying a corresponding ester, e.g. using KOH or NaOH in methanol.

(e) compounds in which X is trans —CH=CH— may be prepared by isomerising the corresponding cis compound. The isomerisation may be effected by treatment with, for example, p-toluene sulphinic acid in dioxan (e.g. at reflux) or azobisisobutyronitrile and thiophenol, using for example a hydrocarbon solvent and any suitable temperature up to reflux. Where an oxo group is desired in the end product, it should be introduced after this reaction.

(f) Compounds in which X is —(CH$_2$)$_2$— may be prepared by catalytic hydrogenation of a corresponding compound in which X is —CH=CH—. Conventional catalysts may be used, preferably palladium or platinum on carbon, in a suitable solvent (e.g. an alcohol such as methanol) e.g. at room temperature.

(g) Compounds of formula (1a) may be prepared by etherification of the corresponding hydroxy compound (in which $R^4$ represents hydrogen), for example by reaction with an appropriate halide ($R^4$ Hal), for example by reaction at room temperature in the presence of a suitable base (e.g. sodium hydride) in a suitable solvent (e.g. dimethylformamide).

Any other hydroxy group present in the starting material (e.g. the ring hydroxy group) should be protected in this reaction.

Starting materials for this reaction may be prepared by the same general technique as described above for process (a), using intermediates in which the group —OR$^4$ is a protected hydroxy group and removing the protecting group prior to etherification.

Starting materials of the formula (4)

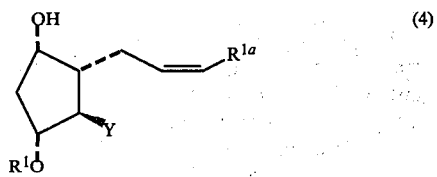

(where $R^{1a}$ is as defined above and —OR$^h$ represents a protected hydroxy group) may also be prepared by method (b) of British Patent Specification 2028805A.

(h) Compounds having ring type (a) can be prepared by removing the protecting group from the corresponding compound in which the ring hydroxy group is protected, for example by reduction or acid or alkaline hydrolysis. This is discussed below in connection with hydroxy group protection.

(i) Compounds of formula (1a) in which Y is a substituted amino group may be prepared by substitution of the corresponding compound in which Y is —NH$_2$.

This reaction may be performed by treating the starting material with a compound of the formula J$R^{13}$J, where J is a readily displaceable group (such as halo, e.g. iodo, or hydrocarbylsulphonyloxy, e.g. p-toluenesulphonyloxy) and $R^{13}$ is the appropriate divalent group (e.g. —(CH$_2$)$_2$O(CH$_2$)$_2$—). The reaction may be carried out in a solvent such as acetonitrile or methanol, in the presence of a suitable base, e.g. potassium carbonate or sodium bicarbonate.

Alternatively, the starting material may be reacted with an appropriate dialdehyde or diketone in the presence of a reducing agent. For example, reaction with glutardialdehyde gives a compound in which Y is piperidino. The reducing agents which may be used are those generally known for the reduction of imines, e.g. formic acid, or an alkali metal borohydride or cyanoborohydride (e.g. sodium borohydride or potassium cyanoborohydride, using an alcohol such as ethanol as solvent, suitably at room temperature, preferably at pH 4-6), or hydrogen in the presence of a metal catalyst, e.g. palladium.

The amines required as starting materials may be prepared by reduction of the corresponding azide, for example as described for process (j).

(j) compounds of ring type (a) in which Y is —NH$_2$ and R$^{10}$ is hydrogen may be prepared by reducing the corresponding compound in which Y represents an azido group.

Compounds in which X is —(CH$_2$)$_2$— may thus be prepared by catalytic hydrogenation, using for example platinum or palladium on carbon as the catalyst. However, when compounds in which X is —CH=CH— are required, selective reduction methods specific for the azide function should be used. Examples of suitable reagents are zinc and sodium dihydrogen phosphate in a suitable solvent (e.g. tetrahydrofuran); zinc and methanol/sulphuric acid; or triphenyl phosphine followed by methanol/sulphuric acid.

The azido starting materials required for this reaction may be prepared by methods analogous to those for preparing the compounds of formula (2), using reagents in which Y is axido. These methods are analogous to those of process (c) of British Patent Specification No. 2028805A.

(k) Salts of the compounds of formula (1) may be prepared by conventional methods, e.g. by treatment with an acid or (where R$^{10}$ is hydrogen) a base in a suitable solvent e.g. water or an organic solvent such as ether.

In the preparation of compounds of formula (1) the ring hydroxy group (or any other hydroxy group present) will often be protected and its liberation will frequently be the last step in the preparation. Conventional methods of protection may be used, protection in the form of t-butyldimethylsilyloxy or tetrahydropyranyloxy groups being preferred. These groups may be removed by acid hydrolysis. The group may also be protected in the form of an alkanoyloxy group having up to 7 carbon atoms, e.g. acetoxy. Such groups may be removed by alkaline hydrolysis.

The examples below illustrate the invention. The preparation of the intermediates required is described first.

The preparation of the following intermediates is described in British Patent Specification 2028805 A:

Intermediate 4:
(±)-3-endo-Hydroxy-2-exo-(4-morpholinyl)bicyclo[3.2.0]-heptan-6-one Intermediate 5:
(3aα,4 α,5β,6aα)-(±)-Hexahydro-5-hydroxy-4-(4-morpholinyl)-2H-cyclopenta(b)furan-2-one Intermediate 6:
(3aα,4α,5β,6aα)-(±)-Hexahydro-4-(4-morpholinyl)-5-(tetrahydro-2H-pyran-2-yl)oxy-2H-cyclopenta(b)furan-2-one Intermediate 7:
(3aα,4α,5β,6aα)-(±)-Hexahydro-4-(4-morpholinyl)-5-(tetrahydro-2H-pyran-2-yl)oxy-2H-cyclopenta(b)furan-2ol Intermediate 8: [1α(Z),2β,3α,5α]-(±)-Methyl 7-[5-Acetoxy-2-(4-morpholinyl)-3-[(tetrahydro-2H-pyran-2-yl)oxy]cyclopentyl]-5-heptenoate Intermediate 9: [1α(Z),2β,3α,5α]-Methyl 7-[5-Hydroxy-2-(4-morpholinyl)-3-[(tetrahydro-2H-pyran-2-yl)oxy]cyclopentyl]-5-heptenoate Temperatures are in °C. The following abbreviations are used:

TLC - thin layer chromatography, PE - petroleum ether (boiling at 40-60° unless otherwise stated), THF -tetrahydrofuran, EA - ethyl acetate, PTSA - p-toluene-sulphonic acid monohydrate, DMF - dimethylformamide, DMSO - dimethylsulphoxide, Dibal - diisobutylalaluminium hydride.

Chromatography was carried out using silica gel. TLC was caried out using SiO$_2$. The following abbreviations illustrate the eluent used for the chromatography and TLC: (A) 9:1 PE(b.p. 60–80°) - EA; (B) 4:1 PE (b.p. 60–80°) - EA; (C) 3:1 PE-ether; (D) ether-EA; (E) 9:1 EA-PE; (F) ether-PE; (G) 4:1 ether-PE; (H) 7:3 ether-PE; (I) 9:1 ether-methanol; (J) ether; (K) EA; (L) 19:1 ether-methanol; (M) 1:1 ether-PE (b.p. 60–80°); (N) 9:1 EA-PE (b.p. 60–80°); (O) EA-PE (b.p. 60–80°); (P) 19:1 EA-methanol; (Q) 95:5 ether-methanol; (R) 85:15 EA-methanol; (S) 3:1 EA-methanol; (T) 98:2 chloroform-methanol; (U) 95:5 EA-methanol; (V) 4:1 ether-methanol; (W) PE; (X) 9:1 EA-methanol; (Y) 7:3 EA-PE; (Z) 3:2 ether-PE; (AB) 1:1 EA-PE; (AC) 4:1 ether-isopentane; (AD) 39:1 ether-methanol; (AE) 4:1 ether-PE (b.p. 60–80°); (AF) ether-isopentane; (AG) chloroform; (AH) 97:3 chloroform-methanol; (AI) 7:3 EA-PE (b.p. 60–80°); (AJ) 85:15 ether-methanol; (AK) 97:3 ether-methanol; AL 99:1 ether-methanol; (AM) ether-methanol.

INTERMEDIATE 12

(±)-7-anti-(4-Morpholinyl)-5-endo-[tetrahydro-2H-pyran-2-yl)oxy]bicyclo[2.2.1]heptan-2-one Morpholine (76 ml) was added dropwise over 15 mins to a stirred solution of 2-exo-bromo-3-endo-[(tetrahydro-2H-pyran-2-yl)oxy]bicyclo[3.2.0]heptan-6-one (100.8g) in acetone (500 ml) at 0°. After 2h at 5° the mixture was stirred at 20° for 18h and then filtered. Evaporation of the filtrate gave an oil which was taken into ether (350 ml), filtered and washed (water, 2×100 ml). The ethereal solution was dried (MgSO$_4$), filtered and evaporated to give the title compound as a solid. Purification from PE gave material (85.5 g) of m.p. 86°–88°.

INTERMEDIATE 14

4-(1,3-Dioxolan-2-yl)-2-phenylthiophene

A solution of 5-bromo-3-thiophenecarboxaldehyde (32.5g) in benzene (500 ml) was treated with PTSA (0.323g) and ethylene glycol (21.1g), and the mixture heated under reflux in a Dean and Stark apparatus until the theoretical volume of water had been removed. After cooling the mixture was washed with water, (2x) then brine, dried (MgSO$_4$), filtered and concentrated, and the residue distilled (b.p. 96°-100° at 0.4 mm) to give the title compound as an oil (24 g).

Analysis Found: C, 35.8; H, 3.0; C$_7$H$_7$BrO$_2$S requires: C, 35.7; H, 3.0%.

INTERMEDIATE 15

(a) 5-Phenyl-3-thiophenecarboxaldehyde

A solution of phenylmagnesium chloride in THF (82.94 ml, 2.39 M) was added to a stirred solution of $ZnBr_2$ (44.6g) in dry THF (350 ml) under nitrogen. The mixture was stirred at room temperature for 15 min.

Dibal (9.91 ml, 1 M) in hexane solution was added dropwise to a stirred mixture of triphenylphosphine (10.39 g) and nickel acetoacetonate (2.55 g) in dry THF (160 ml) under nitrogen. A solution of Intermediate 14 (23.3 g) in dry THF (150 ml) was added after 10 min. The solution containing the organozinc reagent was then added dropwise and the mixture was stirred for 1h.

2N Hydrochloric acid (400 ml) was added at 0° and the mixture was stirred at room temperature for 0.5h. The two layers were separated and the aqueous layer was extracted with ether (2×400 ml), washed with $NaHCO_3$ solution and brine and then dried ($MgSO_4$). Solvent removal in vacuo gave a solid (32.8g) which was chromatographed (A) to give the title compound (13.35 g), m.p. 64°–65° (from PE (b.p. 60°–80°)).

The following compounds were prepared by a similar procedure:

(b) 4-(4-Methoxyphenyl)-2-thiophenecarboxaldehyde, m.p. 75°–76.5° (from PE (b.p. 60°–80°)-EA, 2:1), from 4-bromo-2-(1,3-dioxolan-2-yl)thiophene and p-methoxyphenyl zinc bromide [from 4-bromoanisole, zinc bromide]

(c) 4-(Phenylmethyl)-2-thiophene carboxaldehyde, from 4-bromo-2-(1,3-dioxolan-2-yl)thiophene and a solution of activated zinc dust and benzyl bromide in dry THF. Purification by chromatography (B)

Analysis Found: C, 71.3; H, 5.0; $C_{12}H_{10}OS$ requires: C, 71.3; H, 5.0%.

INTERMEDIATE 16

4-(4-Methoxyphenyl)-2-thiophenemethanol

Intermediate 15(b) (9.85 g) in THF (40ml) and absolute ethanol (160 ml) was stirred with $NaBH_4$ (1.9 g) at room temperature for 1h. Saturated aqueous $KH_2PO_4$ (60 ml) was added and the mixture evaporated in vacuo. Extraction of the residue with $CH_2Cl_2$ (3×50 ml), drying ($MgSO_4$) and evaporation gave a solid. Crystallisation from EA gave the title compound (7.49 g), m.p. 136.5°–138°.

INTERMEDIATE 17 (a)

5-Phenyl-3-thiophenemethanol

A stirred solution of Intermediate 15 (12g) in methanol (120 ml) was treated with $NaBH_4$ (1.82 g) at room temperature for 15 min. The mixture was cooled to 0° and treated with $NH_4Cl$ solution (200 ml), followed by water (200 ml) and ether (400 ml). The ether extract was separated and the aqueous phase further extracted with ether (400 ml), washed with brine, dried ($MgSO_4$), filtered and evaporated to afford the title compound as a solid (11.5 g), m.p. 92°–93°.

(b) 4-(Phenylmethyl)-2-thiophene methanol, m.p. 33°–34° was prepared by a similar procedure from Intermediate 15(c).

INTERMEDIATE 18

2-(1-Cyclohexenyl)thiophene n-Butyllithium (40.7 ml, 1.5 M) was added dropwise to a stirred solution of thiophene (5 g) in dry ether (50 ml) and the mixture heated under reflux for 30 min. After cooling to −78°, cyclohexanone (6.21 ml) in dry ether (30 ml) was added dropwise and the temperature allowed to rise to ambient. After 1h 2N hydrochloric acid (80 ml) was added and stirring continued for 16h. The organic layer was separated and the aqueous layer extracted with ether (2×40 ml). The combined extracts were washed with water, dried ($MgSO_4$), filtered and evaporated to give an oil, which was dissolved in benzene (50 ml) and heated under reflux in the presence of PTSA for 0.75h. the cooled solution was washed twice with 8% $NaHCO_3$ solution and the aqueous solution extracted with ether (2×40 ml), dried ($MgSO_4$) filteed and evaporated to give the title compound as an oil (9.83 g). TLC(F) $R_f$ 0.73

IMTERMEDIATE19

2-Cyclohexylthiophene

A solution of Intermediate 18 (9.8 g) in absolute alcohol (75 ml) was hydrogenated over prereduced 10% palladium oxide on charcoal (2 g). The mixture was filtered ('Hyflo') and the filtrate evaporated. Distillation of the residue gave the title compound (6.6 g) of b.p. 70°–80°/0.2 mm.

INTERMEDIATE °

5-Cyclohexyl-2-thiophenemethanol n-Butyllithium (25.3 ml, 1.5 M) was added dropwise to a stirred solution of Intermediate 19 (6 g) in dry THF (75 ml). After 15 min the solution was cooled to 0° and paraformaldehyde (3.25 g) was added. After a further 20 min at room temperature saturated $NH_4Cl$ solution (30 ml) was added, the organic layer separated and the aqueous solution extracted with ether (2×50 ml), dried ($MgSO_4$), filtered and evaporated, and the residue chromatographed (C). The title compound was obtained as a solid (5.36 g), m.p. 31°–31.5°.

INTERMEDIATE 21

(a) 4-Phenyl-2-thiophenemethanol

A stirred suspension of 4phenyl-2-thiophenecarboxaldehyde (4.32 g) in absolute ethanol (85 ml) was cooled in an ice-bath and treated with $NaBH_4$ (1.06g). After 20 min. the mixture was allowed to attain ambient temperature when stirring was continued for 6h. Saturated aqueous $NH_4Cl$ (30 ml) was then carefully added to the vigorously stirred mixture, and the resulting suspension extracted with ether (2×200 ml). The combined extracts were dried ($Na_2SO_4/K_2CO_3$), filtered and evaporated to give the title compound (4.2 g) as crystals, m.p. 112°–113°.

(b) 4-Bromo-2-thiophene methanol was similarly prepared from 4-bromo-2-thiophene carboxaldehyde.

Analysis Found: C, 31.1; H, 2.6; $C_5H_5BrOS$ requires: C, 30.8; H, 2.6%.

INTERMEDIATE 22

4-Methyl-2-thiophenemethanol

A solution of 4-methyl-2-thiophene carboxylic acid (6 g) in dry ether (50 ml) was added to a stirred suspensin of $LiAlH_4$ (2 g) in dry ether (100 ml) and the mixture kept at room temperature for 2h and 30° for 1h. Wet THF (50 ml) was cautiously added followed by 1N hydrochloric acid (150 ml). The layers were separated and the aqueous solution extracted with ether (100 ml), washed with $Na_2CO_3$ solution (2x), water (2x), brine and then dried ($MgSO_4$). Evaporation gave a liquid which was distilled (b.p. 90°/1 mm) to give the title compound (4.25 g).

INTERMEDIATE 23

(a) 2-(Bromomethyl)-4-phenylthiophene

A cooled, stirred suspension of Intermediate 21a) (3.86 g) in dry $CH_2Cl_2$ (60 ml) was treated dropwise with a solution of $PBr_3$ (1.27 ml) in dry $CH_2Cl_2$ (20 ml), and stirring continued for 30 min. The mixture was treated with 8% aqueous $NaHCO_3$ (100 ml), stirred for 20 min., extracted with ether (1×150 ml, 1×50 ml), and the extracts dried ($MgSO_4$), filtered and evaporated to give the title compound (5.01 g) as a solid, m.p. 87°–88.5°.

The following compounds were prepared by a similar procedure:

(b) 2-Bromomethyl-4-(phenylmethyl)thiophene, from Intermediate 17b); TLC (M) $R_f$ 0.58.

(c) 2-Bromomethyl-5-cyclohexylthiophene, from Intermediate 20; TLC (M) $R_f$ 0.72.

(d) 4-Bromo-2-(bromomethyl)thiophene, from Intermediate 21b),
Analysis Found: C, 23.5; H, 1.6. $C_5H_4Br_2S$ requires: C, 23.5; H, 1.6%.

(e) 2-(Bromomethyl)-4-(4-methoxyphenyl)thiophene, from Intermediate 16;
Analysis Found: C, 50.6; H, 4.1. $C_{12}H_{11}BrOS$ requires: C, 50.9; H, 3.9%.

(f) 4-(Bromomethyl)-2-phenylthiophene, from Intermediate 17; TLC (J) Rf 0.58.

(g) 2-Bromomethyl-4-methylthiophene, from Intermediate 22; TLC (O) Rf 0.55.

INTERMEDIATE 24

2-(Bromomethyl)-5-phenylthiophene

To a boiling solution of 2-methyl-5-phenylthiophene (2g) in dry $CCl_4$ (100 ml) was rapidly added N-bromosuccinimide (1.94 g) and dibenzoylperoxide (0.15 g). After heating under reflux for 30 min., the mixture was cooled and filtered. Evaporation in vacuo gave the title compound as an oil (1.5 g).

Analysis Found: C, 52.0; H, 3.4; $C_{11}H_9BrS$ requires; C, 52.2; H, 3.6%

Intermediate 25

(±)-5-endo-Hydroxy-7-anti-(4-morpholinyl)bicyclo[2.2.1] heptan-2-one, hydrochloride To a stirred solution of Intermediate 12 (96.4 g) in methanol (600 ml) was added an ethereal solution of HCl (240 ml) and the mixture stirred at 20° for 2.5 h (pH 1.5–2). Filtration followed by evaporation of the filtrate gave an oil which solidified on trituration with EA (2×200 ml). Coloured impurities were removed by extraction with boiling isopropanol to leave the title compound as a solid (70.6 g), m.p. 181°–182°.

Intermediate 26

(a) (±)-5-endo-(4-Bromophenylmethoxy)-7-anti-(4-morpholinyl)bicyclo[2.2.1]heptan-2-one Aqueous NaOH solution (10N; 200 ml) was added

Intermediate 26

(c) 7-anti-(4-Morpholinyl)-5-endo-[(5-phenylthien-2-yl)methoxy]bicyclo[2.2.1]heptan-2-one A mixture of 10N NaOH (10 ml), benzyltriethylammonium chloride (0.145 g), Intermediates 25 (0.68 g) and 24 (1.5 g) in $CH_2Cl_2$ (10 ml) was stirred at room temperature for 2 days. Water (10 ml) was added and the aqueous layer extracted with $CH_2Cl_2$ (3×25 ml), dried ($MgSO_4$), filtered and evaporated and the residue purified by chromatography (F) to give the title compound as a solid (0.9 g), m.p. 129°–130°.

The following compound was similarly prepared:

(d) 5-endo-[(5-Cyclohexylthien-2-yl)methoxy]-7-anti-(4-morpholinyl)bicyclo[2.2.1]heptan-2-one, m.p. 56°–57°, from Intermediates 25 and 23(c). Purification by chromatography (G)

INTERMEDIATE 27

(b) 8-anti-(4-Morpholinyl)-6-endo[(5-phenylthien-2-yl)methoxy]-2-oxabicyclo[3.2.1]octan-3-one Peracetic acid (6.1M, 1.93 ml) was added dropwise to a mixture of Intermediate 26(c) (0.9 g) and $CH_3COONa.3H_2O$ (0.96 g) in acetic acid (8 ml) and water (4 ml) at 5°–10°. The resulting mixture was stirred at 20° for 48 h when excess fo peracid was destroyed with 10% $Na_2SO_3$ solution (20 ml). After 1.5 h the solvents were removed in vacuo, the residue taken up into water (20 ml), treated with $Na_2CO_3$ solution until pH 9 and extracted with EA (3×20 ml). The combined extracts were dried ($MgSO_4$), filtered and concentrated, and the residue purified by chromatography (H) through to (I). The title compound was obtained as a solid (0.28 g), m.p. 135°–137°.

The following compound was similarly prepared: (c) 6-endo-[(5-Cyclohexylthien-2-yl)methoxy]-8-anti(4-morpholinyl)-2-oxabicyclo[3.2.1]octan-3-one, from Intermediate 26(d). TLC ($SiO_2$) Ether $R_f$ 0.38. Purification by chromatography (J)

INTERMEDIATE 34

(a) (1α,2β,3α,5α)-(±)-3-Hydroxy-2-(4-morpholinyl)-5-[(5-phenylthien-2-yl)methoxy]cyclopentane acetaldehyde A stirred solution of Intermediate 28(b) (0.5 g) in dry $CH_2Cl_2$ (20 ml) at −70° under nitrogen was treated dropwise with Dibal (1M in hexane, 2.5 ml). After 1 h at −70°, methanol (20 ml) was added and the temperature of the mixture allowed to rise to ambient over 3 h. The mixture was filtered through 'Hyflo', concentrated and the residue taken up into $CH_2Cl_2$ (100 ml). After drying ($MgSO_4$), filtration and concentration gave the title compound as a foam (0.4 g). IR ($CHBr_3$) 1715 cm$^{-1}$.

(b) [1α,2β,3α,5α]-(±)-5-[(5-Cyclohexylthien-2-yl-methoxy]-3-hydroxy-2-(4-morpholinyl)cyclopentane acetaldehyde, was prepared by a similar procedure from Intermediate 28(c), IR ($CHBr_3$) 3580–3530 (broad), 1710 cm$^{-1}$.

INTERMEDIATE 36

(a) [1α(Z),2β,3α,5α]-(±)-Methyl 7-[2-(4-Morpholinyl)-5-[[4-phenylmethyl)thien-2-yl]methoxy]-3-[(tetrahydro-2H-pyran-2-yl)oxy]cyclopentyl]-5-heptenoate.

Sodium hydride (1.34 g, 50% in oil) was added to a stirred solution of Intermediates 9 (3.83 g) and 23(b) (7.75 g) in dry DMF (20 ml) at 0° under nitrogen. The mixture was stirred at 0° for 15 min and then at room temperature for 1 h, whereupon $NH_4Cl$ solution (100 ml) was added and the pH adjusted to 6.5 with $KH_2PO_4$ solution. The mixture was extracted with ether (3×100 ml), washed with water (2×) and brine and then dried ($MgSO_4$). Evaporation in vacuo gave a residue which was purified by chromatography (M) to give the title compound as an oil (2.1 g).

Analysis Found: C, 67.9; H, 8.1; N, 2.2. $C_{34}H_{47}NO_6S$ requires: C, 68.3; H, 7.9; N, 2.4%.

The following compounds were prepared by a similar procedure:

(b) [1α(Z),2β,3α,5α]-(±)-Methyl 7-[5-[(4-Bromothien-2-yl)methoxy]-2-(4-morpholinyl)-3-[(tetrahydro-2H-pyran-2-yl)oxy]cyclopentyl]-5-heptenoate from Intermediates 9 and 23(a). Purification by chromatography (N)

Analysis Found: C, 55.5; H, 6.7; N, 2.1. $C_{27}H_{40}BrNO_6S$ requires: C, 55.3; H, 6.9; N, 2.4%.

(c) [1α(Z),2β,3α, 5α]-(±)-Methyl 7-[5-[[4-(4-Methoxyphenyl)thien-2-yl]methoxy]-2-(4-morpholinyl)-3-[(tetrahydro-2H-pyran-2-yl)oxy]cyclopentyl]-5-heptenoate from Intermediates 9 and 23(e). Purification by chromatography (O).

Analysis Found: C, 66.6; H, 7.8; N, 2.4. $C_{34}H_{47}NO_7S$ requires: C, 66.5; H, 7.71; N, 2.3%.

EXAMPLE 1

(a) 1α(Z),2β,3α,5α]-(±)-Methyl 7-[3-Hydroxy-2-(4-morpholinyl)-5-(2-thienyl methoxy) cyclopentyl]-5-heptenoate NaH (80% dispersion in oil, 0.72 g) was added to a stirred mixture of Intermediate 9 (2.88 g) and 2-bromomethyl thiophene (3.71 g) in dry DMF (15 ml) at room temperature. After 1.5 h the suspension was poured into saturated $NH_4Cl$ solution (100 ml) and extracted with ether. The combined extracts were dried ($MgSO_4$), filtered and concentrated, and the residual oil was stirred for 0.25 h at room temperature with 10% concentrated $H_2SO_4$ in methanol (25 ml). The solution was neutralised with 8% $NaHCO_3$ solution and then extracted with $CH_2Cl_2$. The combined extracts were dried ($MgSO_4$), filtered and concentrated. The residue was purified by short path column chromatography (T). The title compound was obtained as an oil (1.2 g) IR (Neat) 3410, 1730 cm$^{-1}$. TLC 95:5 chloroform-methanol Rf 0.4.

The following compounds were prepared by a similar procedure.

(b) [1α(Z),2β,3α,5α]-(±)-Methyl 7-[3-Hydroxy-2-(4-morpholinyl)-5-[(2-phenylthien-4-yl)methoxy]cyclopentyl]-5-heptenoate from Intermediates 9 and 23(f). IR (CHBr$_3$) 3590, 1628 cm$^{-1}$. Purification by chromatography (I).

(c) [1α(Z),2β,3α,5α]-(±)-Methyl 7-[3-Hydroxy-2-(4-morpholinyl)-5-(3-thienylmethoxy)-cyclopentyl]-5-heptenoate, from Intermediate 9 and 3-bromomethylthiophene. Purification by chromatography using 1–4% methanol in ether as eluent. IR (CHBr$_3$) 3500, 1735 cm$^{-1}$. TLC (Q) R$_f$0.34.

(d) [1α(Z),2β,3α,5α]-(±)-Methyl 7-[3-Hydroxy-5-[(4-methylthien-2-yl)methoxy]-2-(4-morpholinyl)cyclopentyl]-5-heptenoate, from Intermediates 9 and 23(g). Purification by chromatography (L). IR (CHBr$_3$) 3580 (Broad), 1728 cm$^{-1}$.

(e) [1α(Z),2β,3α,5α]-(±)-7-[3-Hydroxy-2-(4-morpholinyl)-5-[(5-phenylfuran-2-yl)methoxy]cyclopentyl]-5-heptenoic acid, from Intermediate 9 and 2-(bromomethyl)-5-phenylfuran, IR(CHBr$_3$) 3500, 1720, 1700, 1018, 788 cm$^{-1}$. TLC (SiO$_2$) (I) R$_f$0.18. Purification by chromatography (I).

(f) [1α(Z),2β,3α,5α]-(±)-Methyl 7-[3-Hydroxy-2-(4-morpholinyl)-5-[(4-phenylthien-2-yl)methoxy)cyclopentyl]-5-heptenoate, from Intermediates 9 and 23(a), m.p. 78°–80°. Purification by chromatography (K) followed by (U).

EXAMPLE 2

(a) [1α(Z),2β,3α,5α]-(±)-7-[3-Hydroxy-2-(4-morpholinyl)-5-[(5-phenylthien-2-yl)methoxy]cyclopentyl]-5-heptenoic acid A mixture of (4-carboxybutyl)triphenylphosphonium bromide (3.36 g) and potassium t-butoxide (1.7 g) in dry THF (40 ml) was stirred at 20° for 15 min. under nitrogen. A solution of Intermediate 34(a) (0.75 g) in dry THF (20 ml) was added dropwise and stirring continued for a further 45 min. Water (3 ml) was added and the solvent removed in vacuo. The residue remaining was taken up into water (25 ml) and the solution adjusted to pH 12-13 with 2N NaOH. The aqueous solution was extracted with ether (3×15 ml) and then acidified to pH 6.5 with 2N hydrochloric acid. The acid solution was extracted with ether (6×25 ml) and the combined extracts dried (MgSO$_4$), filtered and evaporated to give the title compound as a foam (0.6 g). IR (CHBr$_3$) 3500, 1740, 1705 cm$^{-1}$. TLC 92.5:7.5 CH$_2$Cl$_2$-methanol Rf 0.16.

The following compound was prepared by a similar procedure:

(b) [1α(Z),2β,3α,5α]-(±)-7-[5-[(5-Cyclohexylthien-2-yl)methoxy]-3-hydroxy-2-(4-morpholinyl)cyclopentyl]-5-heptenoic acid, from Intermediate 34(b), IR (Neat) 1720 cm$^{-1}$ (broad), TLC (Q) R$_f$0.33.

EXAMPLE 3

[1α(Z),2β,5α]-(±)-7-[5-[(5-Cyclohexylthien-2-yl)methoxy]-2-(4-morpholinyl)-3-oxocyclopentyl]-5-heptenoic acid, was prepared by the oxidation method of Example 7 from the product of Example 2(b). IR (Neat) 1740, 1710 cm$^{-1}$, TLC (G) R$_f$ 0.27. Purification by chromatography (Z).

EXAMPLE 4

[1α(Z),2β,5α]-(±)-7-[2-(4-Morpholinyl)-3-oxo-5-(2-thienylmethoxy)cyclopentyl]-5-heptenoic acid A mixture of the product of Example 1(a) (1.2 g) and KOH (3.3 g) in methanol (15 ml) and water (7.5 ml) was stirred for 5 h. at room temperature. The methanol was removed in vacuo and the aqueous residue was diluted with water (20 ml) and acidified to pH 6.5 with NaHSO$_4$. Extraction with CH$_2$Cl$_2$ gave, after drying over MgSO$_4$ and concentrating, the crude acid as an oil (0.5 g). To a solution of this acid (0.5 g) in triethylamine (1 g), dry DMSO (3 ml) and CH$_2$Cl$_2$ (5 ml) cooled to $-10°$ was added pyridine-SO$_3$ complex (0.58 g). The solution was stirred for 2 h. during which the temperature was allowed to rise to 15°. Water (10 ml) was added and the CH$_2$Cl$_2$ then removed in vacuo. The mixture was then brought to pH 6 with citric acid followed by extraction with EA. The combined extracts were dried (MgSO$_4$), filtered and concentrated to give an oil (0.4 g) which was purified by short path column chromatography (AB) to give the title compound as an oil (0.24 g). IR (CHBr$_3$) 3490, 1733, 1700 cm$^{-1}$. TLC (T) Rf 0.2.

EXAMPLE 5

[1α(Z),2β,3α,5α]-(±)-Methyl (7-[3-Hydroxy-2-(4-morpholinyl)-5-[[4-(phenylmethyl)-thien-2-yl]methoxy]cyclopentyl]-5-heptenoate A solution of Intermediate 36(a) (2 g) in 9:1 methanol-sulphuric acid (15 ml) was stirred for 2 h at room temperture, whereupon NaHCO$_3$ solution (100 ml) was added. The mixture was extracted with EA (3×70 ml), the extracts washed with brine, dried (MgSO$_4$) and concentrated. The residue was chromatographed (I) to give the title compound as an oil (1.44 g). IR (CHBr$_3$) 3500–3400 (broad), 1728 cm$^{-1}$.

Analysis Found: C, 67.4; H, 7.5; N, 2.7. C$_{29}$H$_{39}$NO$_5$S requires: C, 67.8; H, 7.7; N, 2.7%.

EXAMPLE 6

(a)

[1α(Z),2β,3α,5α]-(±)-7-[3-Hydroxy-2-(4-morpholinyl)-5-[[4-(phenylthien-2-yl)methoxy]cyclopentyl]-5-heptenoic acid A mixture of the product of Example 1(f) (0.915 g) and 2N NaOH (5 ml) in methanol (10 ml) was stirred at room temperature for 16 h. The methanol was removed in vacuo and the residue washed with ether (50 ml), acidified with HCl/phosphate buffer to pH 6.5 and extracted with EA (3×50 ml). The combined extracts were dried (MgSO$_4$) and concentrated to give the title compound as a gum which crystallised (0.88 g) in trituration with ether-EA. m.p. 119.5°–121.5°.

The following compounds were prepared by a similar procedure.

(b) [1α(Z),2β,3α,5α]-(±)-7-[3-Hydroxy-2-(4-morpholinyl)-5-[[4-(phenylmethyl)thien-2-yl]methoxy]cyclopentyl]-5-heptenoic acid, from the product of Example 8. Purification by chromatography (L), IR (Neat) 3370, 1705 cm$^{-1}$, TLC (I) R$_f$ 0.29.

(c) [1α(Z),2β,3α,5α]-(±)-7-[3-Hydroxy-5-[(4-methylthien-2-yl)methoxy]-2-(4-morpholinyl)cyclopentyl]-5-heptenoic acid, from the product of Example 1(m), IR (CHBr$_3$) 3600–3500 broad, 1730, 1705 cm$^{-1}$, TLC (I) R$_f$ 0.23.

EXAMPLE 7

(a)

[1α(Z),2β,3α,5α]-(±)-7-[5-[(4-Bromothien-2-yl)methoxy]-3-hydroxy-2-(4-morpholinyl)cyclopentyl]-5-heptenoic acid.

A stirred solution of Intermediate 36(b) (1.29 g) in methanol (100 ml) was treated wtih concentrated sulphuric acid (3.5 ml) and the mixture stirred at room temperature for 1 h. After quenching by carefully pouring into 8% NaHCO$_3$ solution (250 ml) the methanol was removed and the residue extracted with EA (3×50 ml). The combined extracts were evaporated and the residue was dissolved in a mixture of 2N NaOH (5 ml) and methanol (10 ml) with stirring at room temperature. After 18 h the mixture was evaporated in vacuo and the residue acidified to pH 6.5 with 1M aqueous KH$_2$PO$_4$. Extraction with EA (3×50 ml), drying (MgSO$_4$) and evaporation gave the title compound as a glass (0.98 g). IR (CHBr$_3$) 3580, 3560, 3500, 1725, 1700 cm$^{-1}$ TLC (X) R$_f$ 0.22.

(b) [1α(Z),2β,3α,5α]-(±)-7-[3-Hydroxy-5-[[4-(4-methoxyphenyl)thien-2-yl]methoxy]-2-(4-morpholinyl)cyclopentyl]-5-heptenoic acid, was similarly prepared from Intermediate 36(c), m.p. 95°–100°.

Analysis Found: C, 65.6; H, 7.4; N, 2.7. C$_{28}$H$_{37}$NO$_6$S requires: C, 65.2; H, 7.2; N, 2.7%.

EXAMPLE 8

[1α(Z),2β,3α,5α]-(±)-7-[3-Hydroxy-2-(4-morpholinyl)-5-(3-thienylmethoxy)cyclopentyl]-5-heptenoic acid A solution of the product of Example 1(c) (2.7 g) in methanol (15 ml) and water (7 ml) containing KOH (0.3 g) was stirred at room temperature for 2 hours. The methanol was removed in vacuo, and the aqueous solution acidifed to pH 6.5 with NaHSO$_4$ and extracted with CH$_2$Cl$_2$. The combined extracts were dried (MgSO$_4$), filtered and concentrated, and the residue chromatographed (Q) to give the title compound as an oil (0.65 g). IR (CHBr$_3$) 3500 (br), 1730, 1700 cm$^{-1}$. TLC (Si-O)$_2$) (Q) R$_f$ 0.13. Purification by chromatography (Q).

EXAMPLE 9

(a)

[1α(Z),2β,5α]-(±)-7-[2-(4-Morpholinyl)-3-oxo-5-[4-phenylthien-2-yl)methoxy]cyclopentyl]-5-heptenoic acid Trimethylsilyl chloride (0.24 ml) was added to a solution of the product of Example 6(a) (0.83 g) and triethylamine (0.26 ml) in dry toluene (10 ml) at 0°.

A solution of oxalyl chloride (0.54 ml) in dry toluene (5 ml) was stirred under nitrogen at $-60°$ and treated slowly dropwise with a solution of DMSO (0.44 ml) in dry toluene (5 ml). After stirring for 10 min the mixture was treated dropwise with the above prepared solution of alcohol-silyl ester maintaining the internal temperture between $-50°$ to $-45°$. After a further 15 min triethylamine (2.52 ml) was added and the temperature of the mixture allowed to rise to 0°. Aqueous KH$_2$PO$_4$ (200 ml) and EA (100 ml) were added and after shaking the aqueous layer separated. After further extraction with EA (2×50 ml), washing with phosphate buffer (2×20 ml), drying (MgSO$_4$) and concentration there was obtained a foam. Purification by flash chromatography (J) gave the title compound as a solid (0.44 g), m.p. 114°–116°.

The following compounds were prepared using a similar procedure:

(b) [1α(Z),2β,5α]-(±)-7-[2-(4-Morpholinyl)-3-oxo-5-(3-thienylmethoxy)cyclopentyl]-5-heptenoic acid, from the product of Example 8. Purification by chromatography (H). IR (CHBr$_3$) 3500, 3200–2300 (broad), 1735, 1700 cm$^{-1}$. TLC (Q) R$_f$0.2.

(c) [1α(Z),2β,5α]-(±)-7-[2-(4-Morpholinyl)-3-oxo-5-[[4-(phenylmethyl)thien-2-yl]methoxy]cyclopentyl]-5-heptenoic acid, from the product of Example 6(b). Purification by chromatography (AE). IR (CHBr$_3$) 1738, 1700 cm$^{-1}$ TLC. (J) R$_f$0.3.

(d) [1α(Z),2β,5α]-(±)-7-[5-[(4-Bromothien-2-yl) methoxy]-2-(4-morpholinyl)-3-oxocyclopentyl]-5-heptenoic acid, from the product of Example 7(a). Purification by chromatography (AF). IR (CHBr$_3$) 1738, 1700 cm$^{-1}$ TLC (J) R$_f$0.19.

(e) [1α(Z),2β,5α]-(±)-7-[5-[[4-(4-Methoxyphenyl)thien-2-yl]methoxy]-2-(4-morpholyinl)-3-oxocyclopentyl]-5-heptenoic acid, from the product of Example 7(b). Purification by chromatography (AF). m.p. 107.5°–109°.

Analysis Found: C, 65.6; H, 6.9;N, 2.6. C$_{28}$H$_{35}$NO$_6$ requires: C, 65.5; H, 6.9; N, 2.7%.

(f) [1α(Z),2β,5α]-(±)-7-[5-[(4-Methylthien-2-yl)-methoxy]-2-(4-morpholinyl)-3-oxocyclopentyl]-5-heptenoic acid, from the product of Example (6c). Purification by chromatography (J). IR (CHBr$_3$) 3500, 1735, 1700 cm$^1$ TLC (L) R$_f$0.4.

EXAMPLE 10

[1α(Z),2β,5α]-(±)-7-(2-(4-Morpholinyl)-3-oxo-5-[(5-phenylfuran-2-yl)methoxy]cyclopentyl]-5-heptenoic acid Trimethylsilyl chloride (0.073 ml) was added to a solution of the product of Example (1e) (0.25g) and triethylamine (0.082 ml) in dry toluene (5 ml) at 0°. After stirring for 5 min. the mixture was then added to a mixture of N-chloro-succinimide (0.178g) and dimethylsulphide (0.107) in dry toluene (10 ml) and stirring continued for 45 min. Triethylamine (0.28 ml) was added followed after 5 min. by water (10 ml) and KH$_2$PO$_4$ solution until pH 6. The mixture was extracted with ether (3×20 ml) and the combined extracts washed with brine (50 ml) and dried (MgSO$_4$) Filtration and evaporation gave an oil which was purified by flash chromatography (AI). The titlecompound was obtained as a solid (0.084g), which crystallised from ether, m.p. 91.5°–92.5°.

EXAMPLE 11

[1α(Z), 2β,5α]-(±)-7-[2-(4-Morpholinyl)-3-oxo-5-[(5-phenylthien-2-yl)methoxy]cyclopentyl]-5 -heptenoic acid A solution of the product of Example (2a) (0.48 g) in Analar acetone (15 ml) at −10° was treated with Jones reagent (2.67M, 0.46 ml) and the mixture then stirred at 20° for 2 h. Excess reagent was destroyed with 2-propanol and the suspension then adjusted to pH 6.5 with KH$_2$PO$_4$ solution. The solvent was removed in vacuo and the residue extracted with EA (5×50 ml).

The combined extracts were dried (MgSO$_4$), filtered and concentrated. The residue was purified by column chroamtography (F) followed by (AM), followed by preparative TLC (Merck 5717) using 92.5:7.5 dichloromethane-methanol as eluent to give the title compound as a foam (0.075 g).

IR (CHBr$_3$) 3500, 1740, 1705 cm$^{-1}$. TLC 92.5:7.5 dichloromethane-methanol R$_f$0.35.

EXAMPLE 12

[1α(Z),2β,5α]-(±)-7-[2-(4-Morpholinyl)-3-oxo-5-[(2-phenylthien-4-yl)methoxy]cyclopentyl]-5-heptenoic acid The product of Example (1b) (0.9 g) was stirred with 2N NaOH (5 ml) in methanol (10 ml) for 3h. The methanol was removed in vacuo and KH$_2$PO$_4$ solution added until pH 6.5. The mixture was then extracted with EA (3×15 ml), washed with brine, dried (MgSO$_4$) and concentrated. the product (0.94 g) was oxidised according to the method of Example (11a), except that trimethylsilyl chloride and toluene were used instead of triethylsilyl chloride and CH$_2$Cl$_2$ respectively, to give the title compound (0.31 g), m.p. 111°–112°.

PHARMACEUTICAL EXAMPLES

| Tablets | |
|---|---|
| Direct Compression | Mg/tablet |
| Active ingredient | 100.00 |
| Microcrystalline Cellulose B.P.C. | 298.00 |
| Magnesium Stearate | 2.00 |
| Compression Weight | 400.00 |

The active ingredient is sieved through a 250 m$^{-6}$ sieve, blended with the excipients and compressed using 10.0 mm punches. Tablets of other strengths may be prepared by altering the compression weight and using punches to suit.

| Injection for Intravenous Administration | % w/v |
|---|---|
| Active ingredient | 0.50 |
| Water for injections B.P. to | 100.00 |

Sodium chloride may be added to adjust the tonicity of the solution and the pH may be adjusted to that of maximum stability and/or to facilitate solution of the active ingredient using either dilute acid or alkali.

The solution is prepared, clarified and filled into appropriate sized ampoules sealed by fusion of the glass. The injection is sterilised by heating in an autoclave using one of the acceptable cycles. Alternatively the solution may be sterilised by filtration and filled into sterile ampoules under aseptic conditions. The solution may be packed under an inert atmosphere of nitrogen.

| Inhalation Cartridges | /cartridge |
|---|---|
| Active ingredient (micronised) | 3 mg |
| Lactose B.P. to | 25 mg |

The active ingredient is micronised so that the majority of the particles are between 1m$^{-6}$ and 5m$^{-6}$ in longest dimension and none are greater than 10m−6. The active ingredient is then blended with the lactose and the mix is filled into No. 3 hard gelatin capsules using a suitable filling machine.

British Patent Specification 2028805A referred to above corresponds to U.S. patent application Ser. No. 056416 (Collington et al.) U.S. Pat. No. 4,265,891, which is incorporated herein by reference.

We claim:

1. A compound of the formula

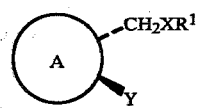

in which
A represents

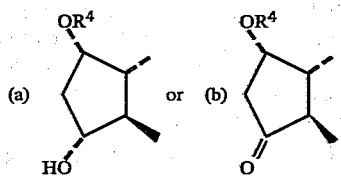

X is cis or trans —CH═CH— or —(CH$_2$)$_2$—;
R$^1$ is straight or branched C$_{1-7}$ alkyl bearing as a terminal substituent —COOR$^{10}$ where R$^{10}$ is a hydrogen atom, C$_{1-6}$ alkyl or C$_{7-10}$ aralkyl;
Y is a saturated heterocyclic amino group which has 5–8 ring members, and optionally contains in the ring one or more —O—, —S—, —SO$_2$—, —NR$^{14}$—, or C(OH)R$^6$ substituents;
wherein R$^{14}$ is a hydrogen atom, C$_{1-7}$ alkyl or aralkyl having a C$_{1-4}$ alkyl portion, R$^6$ is a hydrogen atom, C$_{1-7}$ alkyl, phenyl or aralkyl having a C$_{1-4}$ alkyl portion; and said saturated heterocyclic amino group is optionally substituted by one or more C$_{1-4}$ alkyl groups;

R$^4$ is the group:

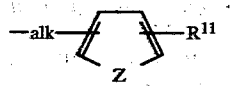

where alk is C$_{1-3}$ alkylene;
Z is O, or S;
R$^{11}$ is a hydrogen atom; C$_{1-6}$ alkyl; C$_{1-6}$ alkoxy; aryl or phenylalkoxy or phenylalkyl having a C$_{1-3}$ alkyl portion, wherein the aryl portion is optionally substituted by C$_{1-3}$ alkyl, C$_{1-3}$ alkoxy or halogen; aryloxy; C$_{5-7}$ cycloalkyl; halogen or nitro; and the physiologically acceptable salts thereof.

2. A compound as claimed in claim 1 in which A is the group (b).

3. A compound of the claim 1 wherein Y is a saturated heterocyclic amino group selected from the group consisting of pyrrolidino, piperidino substituted by hydroxy, morpholino, piperazino, thiamorpholino, 1-dioxothiamorpholino, homomorpholino, or hexamethyleneimino.

4. A compound as claimed in claim 1, 2 or 3 in which X is cis —CH═CH—.

5. A compound as claimed in claim 1, 2 or 3 in which R$^1$ is —(CH$_2$)$_3$COOR$^{10}$ where R$^{10}$ is a hydrogen atom or C$_{1-4}$ alkyl.

6. A compound as claimed in claim 1, 2 or 3 in which R$^4$ is thienylmethyl substituted by phenyl or (C$_{1-3}$ alkoxy) phenyl.

7. A compound as claimed in claim 1, in which:
A is the group (b),
X is cis —CH═CH—,
R$^1$ is —(CH$_2$)$_3$COOH,
Y is morpholino, piperidino or dioxothiamorpholino, and
R$^4$ is methoxyphenylthienylmethyl.

8. A composition comprising a compound as claimed in claim 1, 2, 3 or 7 with one or more pharmaceutical carriers.

* * * * *